United States Patent
Amemiya (10) Patent No.: US 7,351,204 B2
(45) Date of Patent: Apr. 1, 2008

(54) ULTRASONIC DIAGNOSTIC APPARATUS

(75) Inventor: Shinichi Amemiya, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 617 days.

(21) Appl. No.: 10/772,879

(22) Filed: Feb. 5, 2004

(65) Prior Publication Data
US 2004/0158148 A1   Aug. 12, 2004

(30) Foreign Application Priority Data
Feb. 6, 2003   (JP)   ............................. 2003-029405

(51) Int. Cl.
*A61B 8/00*   (2006.01)

(52) U.S. Cl. ....................... 600/437; 600/447

(58) Field of Classification Search ............... 600/437, 600/459, 443, 447, 446; 307/112; 367/138; 377/58; 73/626; 323/234
See application file for complete search history.

(56) References Cited

U.S. PATENT DOCUMENTS

| | | | |
|---|---|---|---|
| 4,092,867 A | | 6/1978 | Matzuk |
| 4,563,899 A | * | 1/1986 | Nakamura ................... 73/626 |
| 4,872,145 A | | 10/1989 | Culbert et al. |
| 5,081,411 A | * | 1/1992 | Walker ....................... 323/326 |
| 5,375,051 A | * | 12/1994 | Decker et al. ................ 363/49 |
| 5,469,484 A | * | 11/1995 | Sato et al. ..................... 377/58 |
| 5,509,413 A | | 4/1996 | Akama et al. |
| 5,542,425 A | | 8/1996 | Marshall et al. |
| 5,592,031 A | * | 1/1997 | Ramos Fernandez et al. ........................... 307/112 |
| 5,610,509 A | | 3/1997 | Nustad |
| 5,640,960 A | | 6/1997 | Jones et al. |
| 5,928,169 A | | 7/1999 | Schatzle et al. |
| 6,310,789 B1 | | 10/2001 | Nebrigic et al. |
| 6,328,697 B1 | * | 12/2001 | Fraser ......................... 600/459 |
| 6,375,619 B1 | | 4/2002 | Ohdachi |
| 6,398,734 B1 | | 6/2002 | Cimochowski et al. |
| 6,499,348 B1 | | 12/2002 | Mamayek |
| 6,572,546 B1 | * | 6/2003 | Bax et al. .................... 600/437 |

(Continued)

FOREIGN PATENT DOCUMENTS

| | | |
|---|---|---|
| JP | 09-093914 | 4/1997 |
| JP | 2002-306475 | 10/2002 |

OTHER PUBLICATIONS

U.S. Patent Application of Shinichi Amemiya, for "Ultrasonic Diagnostic Apparatus and Power Supply Apparatus," U.S. Appl. No. 10/116,476, filed Apr. 4, 2002.

(Continued)

*Primary Examiner*—Eric F. Winakur
*Assistant Examiner*—Michael Rozanski
(74) *Attorney, Agent, or Firm*—Armstrong Teasdale LLP (57) ABSTRACT

For the purpose of reducing the size and power consumption of a power source in an ultrasonic diagnostic apparatus, charge pump circuits are connected to a transmitter power source. A regulator in the transmitter power source drives the charge pump circuit to generate a positive bias voltage +HV2 higher than a positive voltage +HV1 generated by the transmitter power source. The regulator in the transmitter power source also drives the charge pump circuit to generate a negative bias voltage −HV2 lower than a negative voltage −HV1 generated by the transmitter power source.

20 Claims, 6 Drawing Sheets

U.S. PATENT DOCUMENTS

| | | | |
|---|---|---|---|
| 6,635,018 B2 * | 10/2003 | Kawagishi et al. | 600/447 |
| 6,645,145 B1 * | 11/2003 | Dreschel et al. | 600/443 |
| 6,795,374 B2 * | 9/2004 | Barnes et al. | 367/138 |
| 2002/0158299 A1 | 10/2002 | Castro Simas et al. | |
| 2002/0165452 A1 | 11/2002 | Amemiya | |

OTHER PUBLICATIONS

Japanese language Notice of Reasons for Rejection from the Japanese Patent Office, no date.

EP Search Report; Place of Search Munich; Reference No. 16UL145622/9823; App. No. 04250581.8-2220 PCT; 3 pgs, no date.

Takahashi et al.; Complementary Charge Pump Booster; Electronics and Communications in Japan, Part 2, vol. 82, No. 6, 1999; pp. 253-260.

Ioffe; The ins and outs of charge-pump-converter ICs; EDN—Electrical Design News, 44 Jun. 10, 1999, No. 12, Newton, MA, US; pp. 135-142.

* cited by examiner

ULTRASONIC DIAGNOSTIC APPARATUS

CROSS REFERENCE TO RELATED APPLICATIONS

This application claims the benefit of Japanese Application No. 2003-029405 filed Feb. 6, 2003.

BACKGROUND OF THE INVENTION

The present invention relates to an ultrasonic diagnostic apparatus for transmitting ultrasonic signals from ultrasonic transducers toward a subject to be examined, and receiving reflected waves of the ultrasonic signals for display, and more particularly to an ultrasonic diagnostic apparatus of small size and low power consumption.

Conventionally, an ultrasonic diagnosis for imaging the interior of a subject by applying ultrasound to a region to be examined in the subject with an abutting ultrasonic probe, and producing an image of echo signals of reflected waves of the applied ultrasound is commonly used. Since ultrasound is harmless to a living body, the ultrasonic diagnostic apparatus is especially useful for medical applications and is used for detection of foreign material in the living body, determination of lesion degree, observation of a tumor or a fetus, and the like.

In recent years, size and weight reduction of an ultrasonic diagnostic apparatus is desired. An ultrasonic diagnostic apparatus of small size and light weight overall will desirably provide an ultrasonic diagnostic apparatus that can be easily carried. A problem in reducing the size and weight of the ultrasonic diagnostic apparatus is especially in a power source section. Since the ultrasonic diagnostic apparatus requires provision of a transmitter power source for ultrasonic transducers, and in addition, a bias power source for an analog switch, attempts have been made to reduce the size of these power sources.

A conventional method for reducing the size of the power source involves generating transmitter power source from a bias power source for an analog switch (for example, see Patent Document 1).

[Patent Document 1]

Japanese Patent Application Laid Open No. 2002-306475.

In the conventional ultrasonic diagnostic apparatus, however, although size reduction of the apparatus is achieved by combining the transmitter power source and bias power source, a problem of a large power loss arises.

Specifically, since it is necessary for the voltage of the bias power source to be higher than that of the transmitter power source, the conventional ultrasonic diagnostic apparatus is configured to obtain the transmitter power source from the bias power source via a voltage drop circuit (direct current stabilizing power source circuit). In such a configuration, if the voltage supplied from the transmitter power source to the ultrasonic transducers is low, the voltage difference between the bias power source and transmitter power source becomes large, resulting in the large power loss.

Such a power loss leads to a problem of shorter usable time and larger heat generation in a portable ultrasonic diagnostic apparatus in which the ultrasonic transducers are driven by a battery.

SUMMARY OF THE INVENTION

Therefore, an object of the present invention is to provide an ultrasonic diagnostic apparatus comprising a power source of small size and low power consumption.

The present invention of a first aspect for solving the aforementioned problems and attaining the object is an ultrasonic diagnostic apparatus for transmitting ultrasonic signals from ultrasonic transducers toward a subject to be examined, and receiving reflected waves of said ultrasonic signals for display, characterized in comprising: an analog switch for switching ultrasonic transducers for transmission of said ultrasonic signals and reception of said reflected waves; a transmitter power source for supplying a high voltage to a transmitter circuit for causing said ultrasonic transducers to drive said ultrasonic signals; and a bias power source generating circuit for generating a bias power source for said analog switch from said transmitter power source.

According to the invention of the first aspect, in the ultrasonic diagnostic apparatus, a bias power source is generated by a bias power source generating circuit from a transmitter power source for use in transmission of ultrasonic signals, and the power is supplied to the analog switch; and therefore, no separate power source for the bias voltage for the analog switch is needed, and the power source can be reduced in size.

The present invention of a second aspect is characterized in that: in the invention of the first aspect, said bias power source generating circuit comprises a positive bias power source generating circuit for outputting a voltage value higher than a positive voltage value of said transmitter power source; and a negative bias power source generating circuit for outputting a voltage lower than a negative voltage value of said transmitter power source.

According to the present invention of the second aspect, in the ultrasonic diagnostic apparatus, a positive bias power source circuit generates a voltage higher than a positive voltage value of the transmitter power source, and a negative bias power source circuit generates a voltage lower than a negative voltage value of the transmitter power source; and therefore, a bias voltage of sufficient magnitude as compared with the transmission voltage can be obtained.

The present invention of a third aspect is characterized in that: in the invention of the first or second aspect, said positive bias power source generating circuit comprises a positive charge pump circuit that uses the positive voltage of said transmitter power source as a reference; said negative bias power source generating circuit comprises a negative charge pump circuit that uses the negative voltage value of said transmitter power source as a reference; and said bias power source generating circuit uses outputs of said positive charge pump circuit and said negative charge pump circuit as the bias power source for said analog switch.

According to the present invention of the third aspect, in the ultrasonic diagnostic apparatus, a charge pump circuit that uses the positive voltage of the transmitter power source as a reference generates a voltage higher than the positive voltage of the transmitter power source, and a charge pump circuit that uses the negative voltage of the transmitter power source as a reference generates a voltage lower than the negative voltage of the transmitter power source; and therefore, a bias power source for the analog switch is obtained with a simple configuration, and power consumption in the power source is reduced. Accordingly, the ultrasonic diagnostic apparatus is reduced in overall size and reduction in power consumption is achieved.

The present invention of a fourth aspect is characterized in that: in the invention of the first, second or third aspect, said apparatus further comprises a transmission voltage control section for variably controlling the voltage value of said transmitter power source.

According to the present invention of the fourth aspect, the ultrasonic diagnostic apparatus is capable of arbitrarily controlling the transmission voltage by a transmission voltage control section, and the bias voltage is generated based on the transmission voltage; and therefore, power consumption in the power source is minimized. Thus, by applying the present invention to a battery-driven ultrasonic diagnostic apparatus, a portable ultrasonic diagnostic apparatus that can be operated over a long time is obtained.

The present invention of a fifth aspect is characterized in that: in the invention of the third or fourth aspect, a driving circuit for said charge pump shares a driving circuit in said transmitter power source.

According to the present invention of the fifth aspect, the shared use of a driving circuit enables size reduction and high efficiency, and is suitable for a portable ultrasonic diagnostic apparatus.

The present invention of a sixth aspect is characterized in that: in the invention of the first—fifth aspects, said transmitter power source comprises a stabilizing power source circuit for decreasing the positive voltage value supplied to said transmitter circuit, and a stabilizing power source circuit for increasing the negative voltage value supplied to said transmitter circuit.

According to the present invention of the sixth aspect, in the ultrasonic diagnostic apparatus, the transmitter power source can be provided with a voltage drop circuit to reduce noise in the transmission voltage.

According to the present invention, a charge pump circuit is connected to a transmitter power source for generating a voltage supplied to ultrasonic transducers, and an output of the charge pump circuit is employed as a bias power source for an analog switch, and therefore, an effect is obtained that there is provided an ultrasonic diagnostic apparatus having a power source section reduced in size and having reduced power consumption.

Further objects and advantages of the present invention will be apparent from the following description of the preferred embodiments of the invention as illustrated in the accompanying drawings.

DETAILED DESCRIPTION OF THE INVENTION

An ultrasonic diagnostic apparatus in accordance with an embodiment of the present invention will now be described in detail with reference to the appended drawings.

Figure 1:
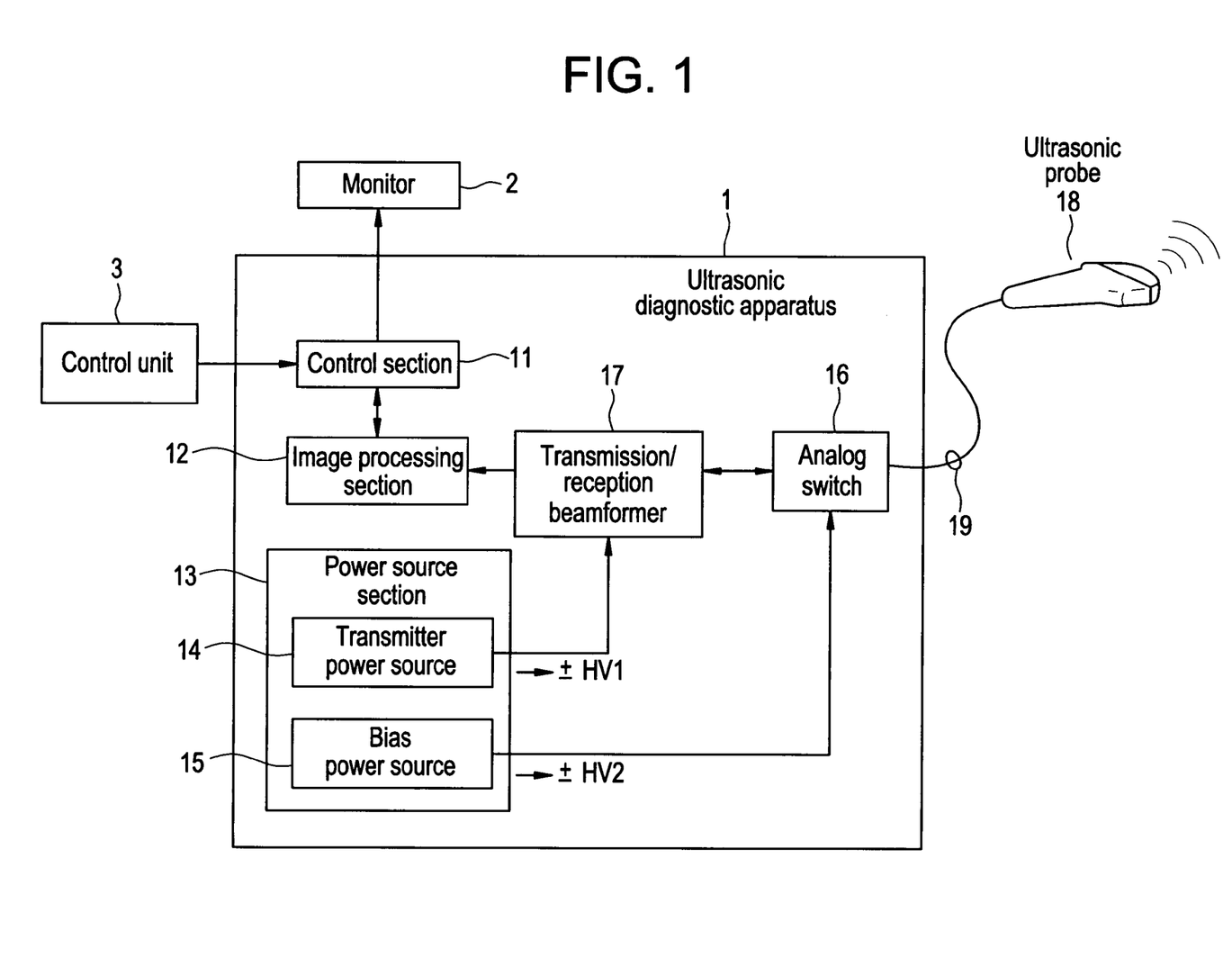
FIG. 1 is an explanatory diagram for explaining the overall configuration of an ultrasonic diagnostic apparatus in accordance with an embodiment of the present invention.

FIG. 1 is an explanatory diagram for explaining the overall configuration of an ultrasonic diagnostic apparatus in accordance with an embodiment of the present invention. In FIG. 1, an ultrasonic diagnostic apparatus 1 is connected to a monitor 2, a control unit 3 and an ultrasonic probe 18. For the monitor 2, any monitor, such as a CRT or liquid crystal monitor, may be used. The control unit 3 may be a general-purpose input device such as a keyboard or mouse, or may be provided with a dedicated console panel.

The ultrasonic diagnostic apparatus 1 also comprises therein a control section 11, an image processing section 12, a power source section 13, an analog switch 16 and a transmission/reception beamformer 17. Moreover, the power source section 13 has therein a transmitter power source 14 and a bias power source 15.

In a diagnosis using the ultrasonic diagnostic apparatus 1, first, transmitter power ±HV1 is supplied from the transmitter power source 14 to the transmission/reception beamformer 17. The transmission/reception beamformer 17 uses the transmitter power source ±HV1 to transmit ultrasonic signals from ultrasonic transducers in the ultrasonic probe 18 connected via the analog switch 16 and a connection cable 19. The ultrasonic transducers then receive reflected waves of the transmitted ultrasonic signals, and input them to the transmission/reception beamformer via the connection cable 19 and analog switch 16.

The transmission/reception beamformer 17 transmits the input reflected waves to the image processing section 12, which produces an ultrasonic image based on the reflected waves. The control section 11 displays on the monitor 2 the ultrasonic image produced by the image processing section 12 based on the input from the control unit 3.

The analog switch 16 conducts switching of ultrasonic transducers to be connected to the transmission/reception beamformer 17. Since ultrasonic transducers for transmitting ultrasonic signals are selected by the switching by the analog switch 16, an area to be examined can be scanned by appropriately operating the analog switch 16.

Figure 2:
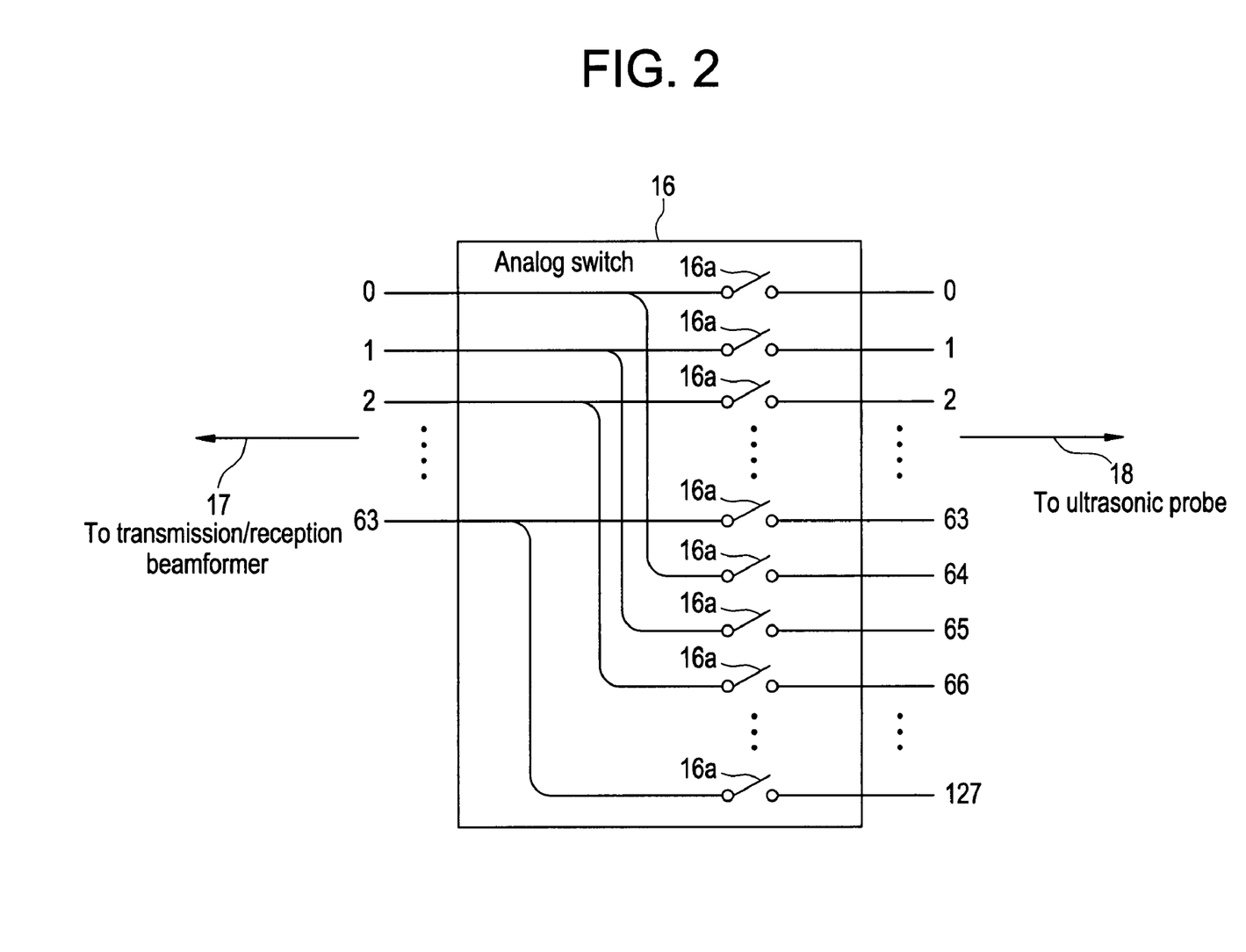
FIG. 2 shows the internal configuration of an analog switch shown in FIG. 1.

FIG. 2 shows the internal configuration of the analog switch 16. As shown, the analog switch 16 comprises therein a plurality of switches 16a. If the transmission/reception beamformer 17 has 63 channels and the ultrasonic probe 18 has 124 ultrasonic transducers, for example, the number of switches 16a included in the analog switch 16 is 124. The analog switch 16 selects ultrasonic transducers to be connected to the transmission/reception beamformer 17 by turning on selected switches 16a. Moreover, the analog switch 16 changes ultrasonic transducers for transmitting ultrasonic signals by changing switches 16a that are turned on, and an ultrasonic scan is thus conducted.

The analog switch 16 is supplied with a bias voltage ±HV2 by the bias power source 15. The bias voltage ±HV2 is in a range that is desirably 10-20V positively and negatively larger than the transmission voltage ±HV1 output by the transmitter power source 14. For example, if the transmission voltage ±HV1 is −100V−+100V, the bias voltage ±HV2 is −120V−+120V.

The amplitude range of the bias voltage ±HV2 is made larger than that of the transmission voltage ±HV1 for preventing an increase of on-resistance in the analog switch 16 due to reduction in bias voltage.

Figure 3:
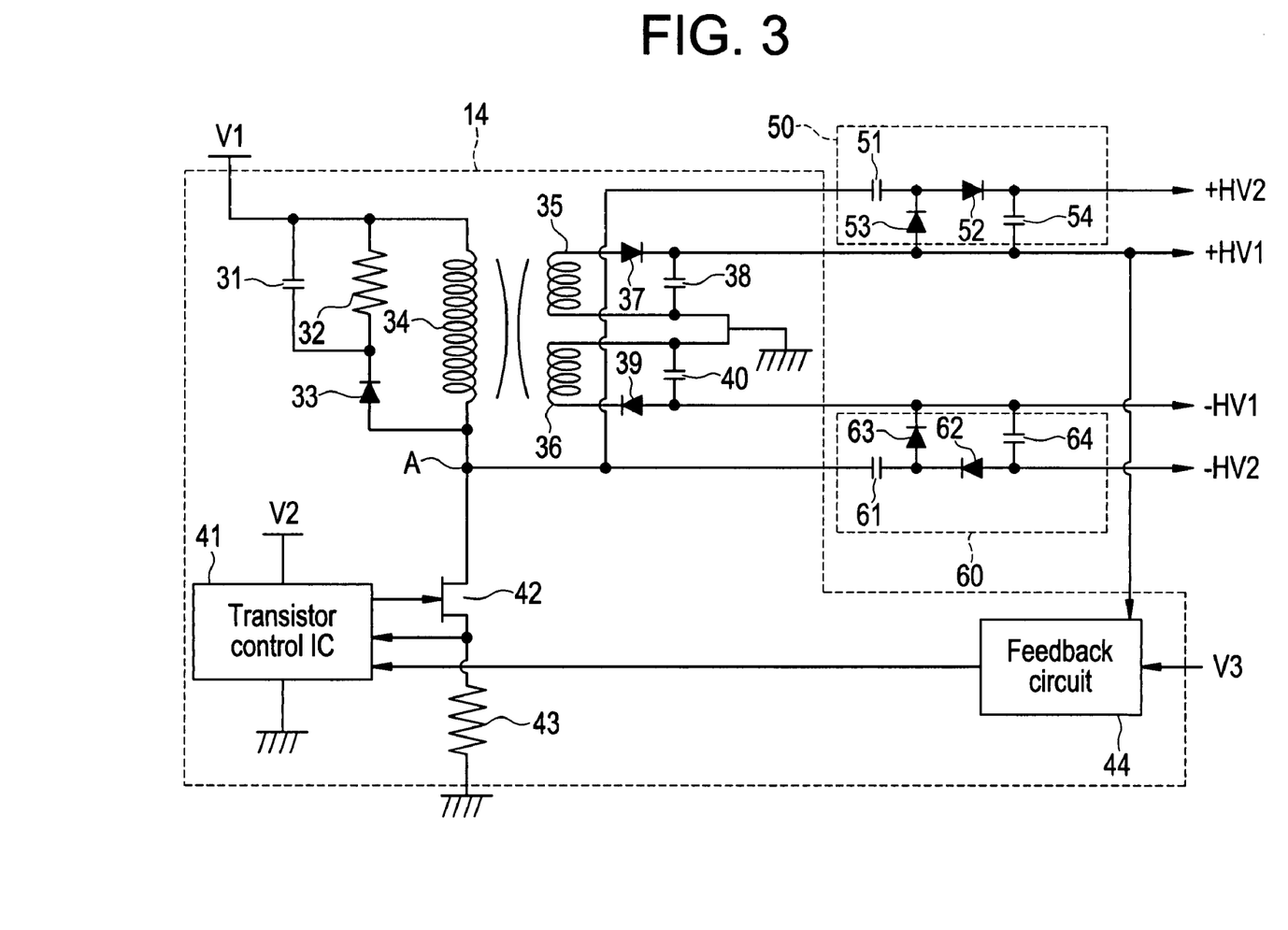
FIG. 3 shows the circuit configuration of a power source section shown in FIG. 1.

Next, a specific configuration of the power source section 13 will be described. FIG. 3 shows a circuit configuration of the power source section 13 shown in FIG. 1. In FIG. 3, the power source section 13 comprises charge pump circuits 50 and 60 connected to the transmitter power source 14, and outputs of the charge pump circuits 50 and 60 are used as the bias power source 15.

Specifically, a regulator circuit comprised of capacitors 31, 38 and 40, diodes 33, 37 and 39, a resistance 32, and inductors 34, 35 and 36 is formed in the transmitter power source 14, and the transmitter power source 14 outputs the transmission voltage ±HV1 from a direct current power source V1.

Moreover, the transmitter power source 14 is controlled by a transistor 42, an SW power source control IC 41, a resistance 43 and a feedback circuit 44. More particularly, the transmission voltage +HV1 and a comparison voltage V3 are input to the feedback circuit 44, which inputs the transmission voltage +HV1 and comparison voltage V3 to the SW power source control IC 41.

On the other hand, the SW power source control IC 41 conducts switching control of the transistor 42 to control the operation of the regulator circuit. By controlling the transistor 42 so that the transmission voltage +HV1 input from the feedback circuit 44 is a constant multiple of the comparison voltage V3, the transmission voltage ±HV1 can be controlled to a desired value. It is thus possible to adjust the ultrasonic signal output transmitted from the ultrasonic transducers to an optimum value by enabling control of the transmission voltage value.

The charge pump circuit 50 is formed from capacitors 51 and 54 and diodes 52 and 53. The charge pump circuit 50 is connected to a point A between the regulator circuit and transistor 42, and driven by the regulator circuit to output a voltage higher than the transmission voltage +HV1 as the positive bias voltage +HV2.

Likewise, the charge pump circuit 60 is formed from capacitors 61 and 64 and diodes 62 and 63. The charge pump circuit 60 is connected to the point A between the regulator circuit and transistor 42, and driven by the regulator circuit to output a voltage lower than the transmission voltage −HV1 as the negative bias voltage −HV2.

By thus adding the charge pump circuits 50 and 60 to the transmitter power source 14 and driving the charge pump circuits 50 and 60 by the regulator in the transmitter power source 14, the bias voltage +HV2 higher than the transmission voltage +HV1 and the bias voltage −HV2 lower than the transmission voltage −HV1 can be obtained.

Desirably, the bias voltage +HV2 is 10-20V higher than the transmission voltage +HV1, and the bias voltage −HV2 is 10-20V lower than the transmission voltage −HV1. Therefore, if a desired bias voltage cannot be obtained by the one-stage charge pump circuit for the transmission voltage ±HV1, a multi-stage configuration in which the charge pump circuit 50 or 60 is connected with an additional charge pump circuit may be employed.

Figure 4:
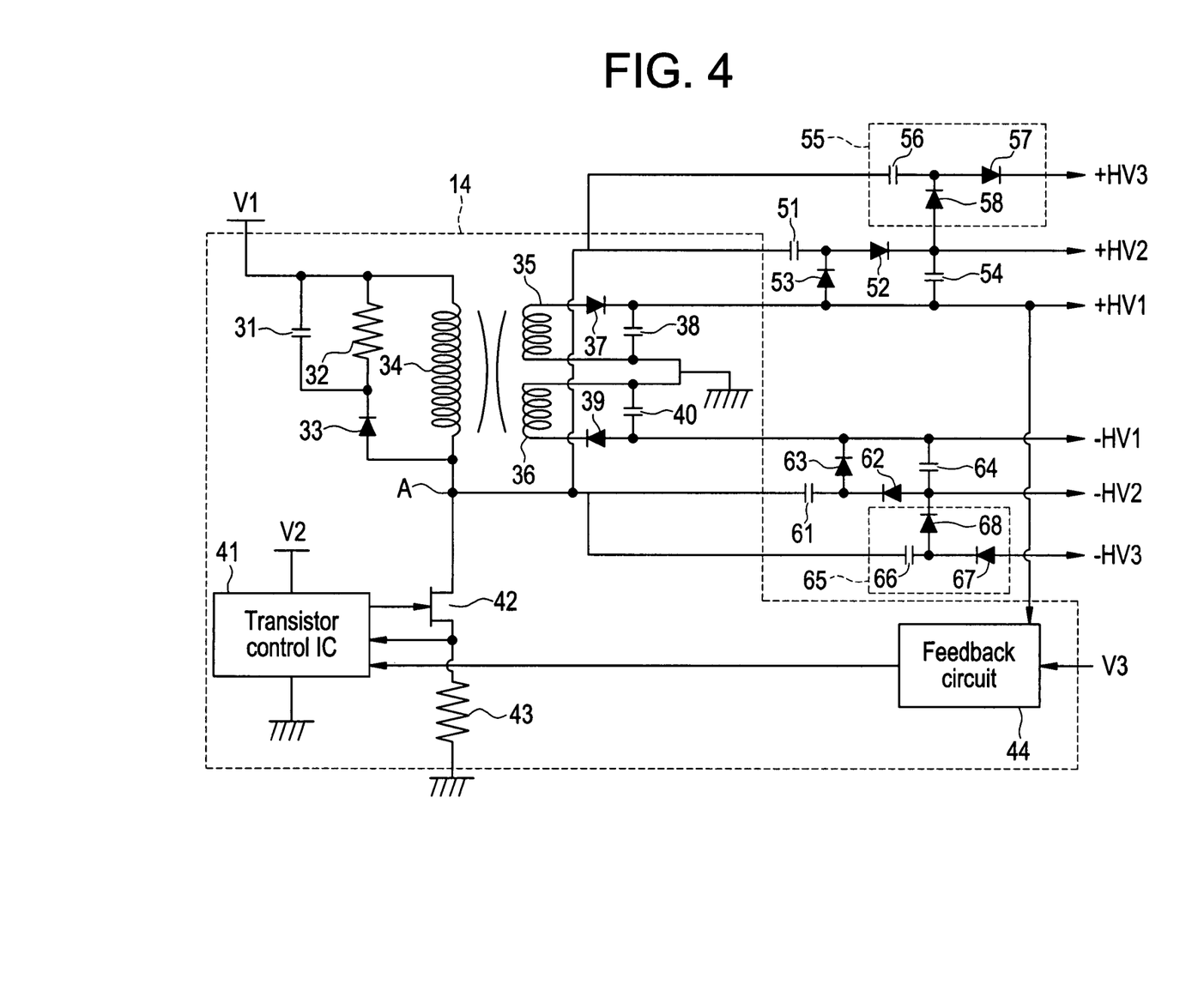
FIG. 4 shows the circuit configuration of a power source section having charge pump circuits of multi-stage configuration.

A circuit configuration of the multi-stage power source section 13 in which the charge pump circuits are connected with additional charge pump circuits is shown in FIG. 4. In the power source section shown in FIG. 4, the charge pump circuit 50 is connected with an additional charge pump circuit 55 and the charge pump circuit 60 is connected with an additional charge pump circuit 65.

Particularly, the charge pump circuit 55 is formed from a capacitor 56 and diodes 57 and 58, and outputs a voltage still higher than the bias voltage +HV2 as a positive bias voltage +HV3. The charge pump circuit 65 is formed from a capacitor 66 and diodes 67 and 68, and outputs a voltage still lower than the bias voltage −HV2 as a negative bias voltage −HV3.

By thus using a multi-stage charge pump in which a charge pump circuit is connected with an additional charge pump circuit, the positive bias voltage can be increased to a desired value and the negative bias voltage can be decreased to a desired value.

Although the charge pump is shown as having a dual-stage configuration in FIG. 4, additional charge pump circuits may be added as needed. Moreover, in FIG. 4, the bias voltage ±HV2 output by the charge pump circuits 50 and 60 and the bias voltage ±HV3 output by the charge pump circuits 55 and 65 are separately output.

Therefore, in the power source circuit shown in FIG. 4, any one of ±HV2 and ±HV3 may be employed as a bias voltage depending upon the required voltage. The selection of the bias voltage can be made by any switching means such as a switch. Moreover, if the value ±HV3 is constantly used as the bias voltage, the switching means and output terminals for ±HV2 are not needed.

Although the charge pump circuits 50 and 60 are connected to the point A between the regulator and transistor in the power source circuit shown in FIG. 3, the connecting position for the charge pumps is not limited to the point A.

Figure 5:
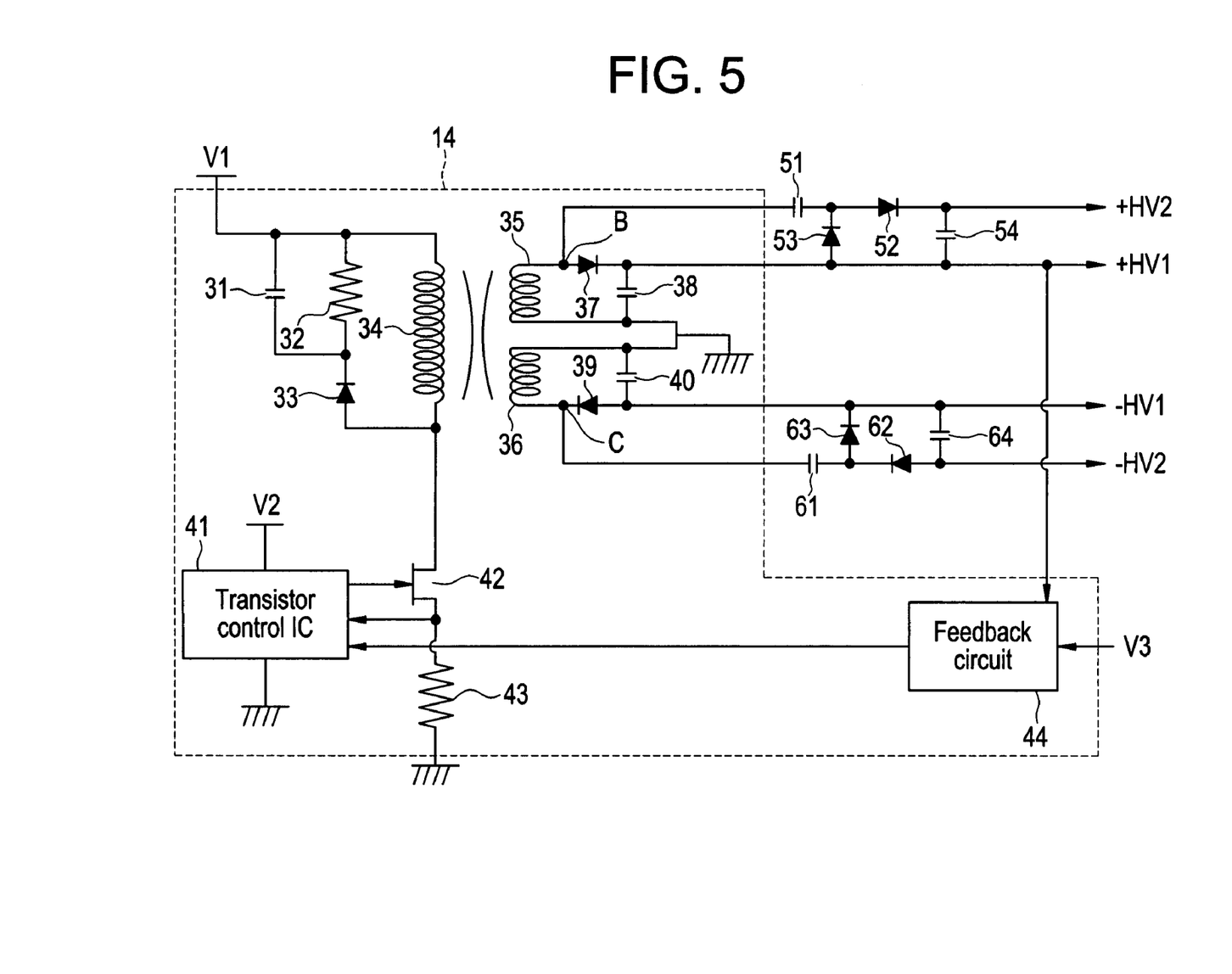
FIG. 5 illustrates variation of the power source circuit shown in FIG. 3.

A variation of the power source circuit is shown in FIG. 5. In FIG. 5, the charge pump circuit 50 is connected to a point B between the inductor 35 and diode 37 in the transmitter power source 14. The charge pump circuit 60 is connected to a point C between the inductor 35 and diode 39 in the transmitter power source 14.

When the charge pump circuit 50 is connected to the point B, its output +HV2 is again sufficiently higher than the transmission voltage +HV1. Similarly, when the charge pump circuit 60 is connected to the point C, its output −HV2 is sufficiently lower than the transmission voltage −HV1. Therefore, points to which the charge pump circuits 50 and 60 are to be connected can be freely designed taking the overall circuit configuration and the like into account.

Next, the output of the transmitter power source 14 will be described. The transmission voltage +HV1 output by the transmitter power source 14 is supplied to the ultrasonic transducers for use in transmission of ultrasonic signals, and therefore, removal of noise from the transmission voltage ±HV1 is important. To remove noise from the transmission voltage ±HV1, a voltage drop circuit or a filter circuit is needed.

Figure 6A:
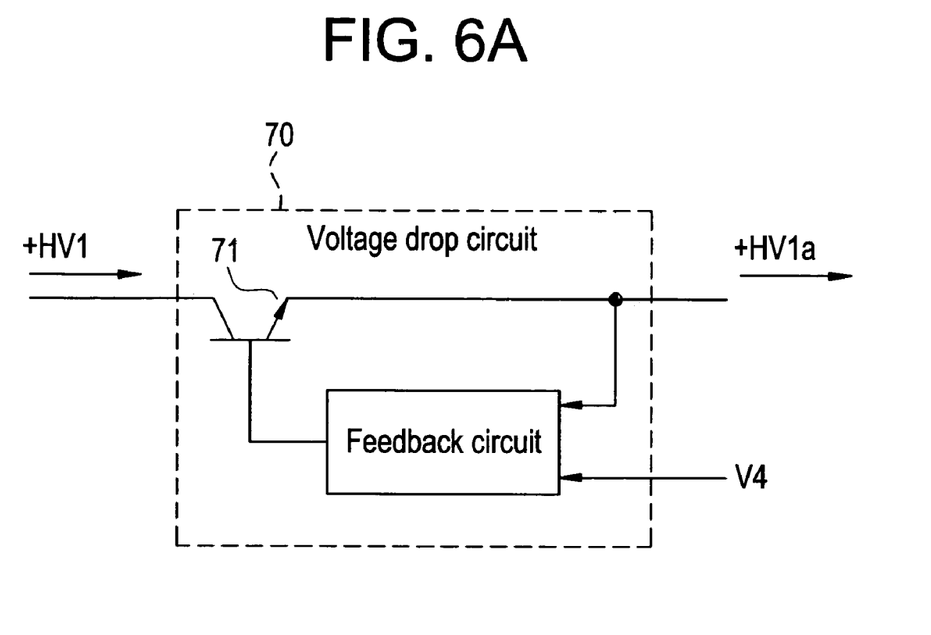
FIG. 6 shows a noise removing circuit for use in the transmitter power source.

FIG. 6 shows an exemplary circuit for use in the noise removal for the transmitter power source 14. FIG. 6(a) is a circuit configuration in which a voltage drop circuit is employed for the noise removing circuit. As shown, the voltage drop circuit 70 is made from a transistor 71 and a feedback circuit 72. The feedback circuit 72 conducts switching control of the transistor 71 with reference to a voltage V4, and the value of voltage +HV1 is reduced by a predetermined amount to output a voltage +HV1a. A similar voltage drop circuit is connected to the voltage −HV1, and the value of voltage −HV1 is increased by a predetermined amount to output a voltage −HV1a.

By supplying the voltage +HV1a and −HV1a to the transmission/reception beamformer 17, power source with lower noise than in supplying the voltage ±HV1 is achieved. Preferably, the difference between the voltages +HV1 and +HV1a is of the order of 3 V.

Figure 6B:
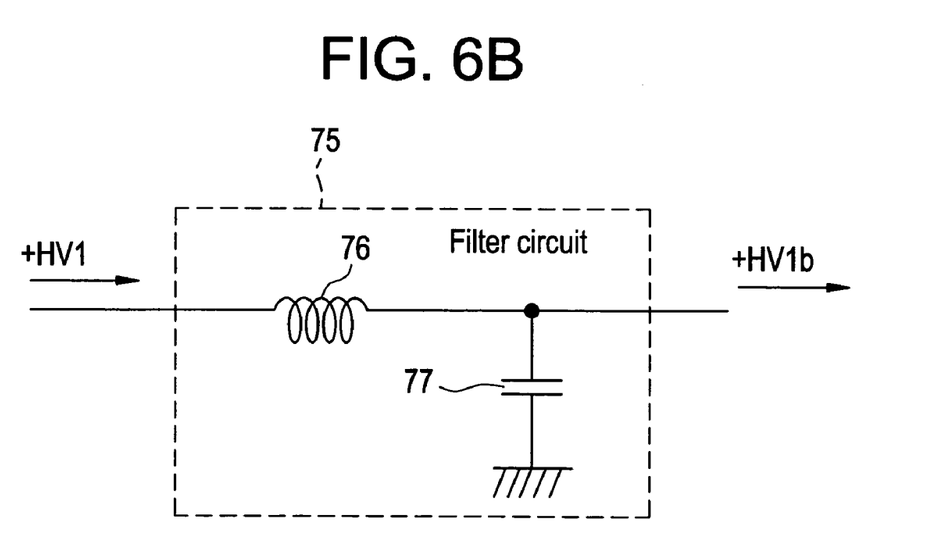

FIG. 6(b) is a circuit configuration in which a filter circuit is employed for the noise removing circuit. As shown, the filter circuit 75 is made from an inductor 76 and a capacitor 77. The filter circuit 75 outputs a voltage +HV1b obtained by removing noise of predetermined frequency from the voltage +HV1. A similar filter circuit is connected to the voltage −HV1, and a voltage −HV1b obtained by removing noise of predetermined frequency from the voltage −HV1 is output.

By supplying the voltage +HV1b and −HV1b to the transmission/reception beamformer 17, power source with lower noise than in supplying the voltage ±HV1 is achieved. The frequency of noise removed by the filter circuit is determined by the inductor 76 and capacitor 77.

As described above, in the ultrasonic diagnostic apparatus in accordance with the present embodiment, the charge pump circuits are connected to the transmitter power source for the transmission/reception beamformer 17, and outputs of the charge pump circuits are employed as a bias power source for the analog switch, and therefore, the power source section is reduced in size and power consumption is reduced.

Moreover, since a charge pump circuit for generating a positive bias voltage and that for generating a negative bias voltage each can be made by two capacitors and two diodes, the power source section can be constructed with a simple configuration and at a low cost. Although a driving circuit for the charge pump may be separately provided, it is possible to use an output of the switching driving circuit in the transmitter power source. Furthermore, a circuit design with a high degree of freedom can be realized by using a multi-stage configuration of the charge pump or changing connection points between the charge pumps and transmitter power source.

In addition, since the low power consumption of such a configuration reduces the amount of heat generation from the power source section, no large cooling means is needed. While cooling means such as forced air cooling is needed if the amount of heat generation from the power source section is large, such cooling means is not needed, and hence, the ultrasonic diagnostic apparatus is further reduced in size.

The size reduction and lowering of power consumption of the power source section itself, and, in addition, the fact that no cooling means is needed, enable the ultrasonic diagnostic apparatus to have smaller overall size and longer battery operation time, and therefore, a small portable ultrasonic diagnostic apparatus can be implemented.

Although the analog switch 16 is provided inside the ultrasonic diagnostic apparatus 1 in the present embodiment, the present invention may be applied without limitation on the position of the analog switch; for example, the analog switch may be provided inside the ultrasonic probe.

Moreover, a charge pump circuit is employed in the present invention. This is because a capacitor used in the charge pump is smaller and cheaper than a small-size transformer. The basic efficacy of the present invention is, however, obtainable by constructing the bias power source from the transmitter power source using the small-size transformer.

Many widely different embodiments of the invention may be configured without departing from the spirit and the scope of the present invention. It should be understood that the present invention is not limited to the specific embodiments described in the specification, except as defined in the appended claim.

The invention claimed is:

1. An ultrasonic diagnostic apparatus for transmitting ultrasonic signals from ultrasonic transducers toward a subject to be examined, and receiving reflected waves of said ultrasonic signals for display, said ultrasonic diagnostic apparatus comprising:

an analog switch for switching ultrasonic transducers for transmission of said ultrasonic signals and reception of said reflected waves;

a transmitter power source comprising a regulator circuit coupled to a power source for supplying a high voltage to a transmitter circuit for causing said transmitter circuit to drive said ultrasonic transducers, said regulator circuit comprising a capacitor, a diode, a resistor, a first inductor, and a second inductor, wherein the first and second inductors are configured such that the first inductor induces a voltage in the second inductor; and a bias power source generating circuit for generating a bias power source for said analog switch from said transmitter power source.

2. The ultrasonic diagnostic apparatus of claim 1, wherein said bias power source generating circuit comprises a positive bias power source generating circuit for outputting a voltage value higher than a positive voltage value of said transmitter power source, and a negative bias power source generating circuit for outputting a voltage lower than a negative voltage value of said transmitter power source.

3. The ultrasonic diagnostic apparatus of claim 2 wherein each of said positive bias power source generating circuit and said negative power generating circuit comprises at least one charge pump circuit.

4. The ultrasonic diagnostic apparatus of claim 1, wherein said circuit for generating said bias power source from said transmitter power source is a charge pump.

5. The ultrasonic diagnostic apparatus of claim 4, wherein a driving circuit for said charge pump shares a driving circuit in said transmitter power source.

6. The ultrasonic diagnostic apparatus of claim 4 wherein said charge pump is coupled between said regulator circuit and a transistor.

7. The ultrasonic diagnostic apparatus of claim 4 wherein said charge pump comprises a plurality of capacitors and a plurality of diodes configured for either generating a positive bias voltage or a negative bias voltage.

8. The ultrasonic diagnostic apparatus of claim 1, wherein said apparatus is a transmission voltage control circuit for variably controlling the voltage value of said transmitter power source.

9. The ultrasonic diagnostic apparatus of claim 8 wherein said transmission voltage control circuit further comprises a transistor and an integrated circuit.

10. The ultrasonic diagnostic apparatus of claim 8 wherein said transmission voltage control circuit further comprises a feedback circuit.

11. The ultrasonic diagnostic apparatus of claim 10 wherein said feedback circuit controls a transistor based on a reference voltage to facilitate controlling a transmission voltage.

12. The ultrasonic diagnostic apparatus of claim 1, wherein
said transmitter power source comprises a stabilizing power source circuit for decreasing and stabilizing the positive voltage value supplied to said transmitter circuit, and a stabilizing power source circuit for increasing and stabilizing the negative voltage value supplied to said transmitter circuit.

13. The ultrasonic diagnostic apparatus of claim 1 further comprising a voltage drop circuit coupled to said transmitter power source.

14. The ultrasonic diagnostic apparatus of claim 13 wherein said voltage drop circuit further comprises a transistor and a feedback circuit.

15. The ultrasonic diagnostic apparatus of claim 14 wherein said feedback circuit controls said transistor using a reference voltage.

16. The ultrasonic diagnostic apparatus of claim 1 further comprising a filter circuit for facilitating removing noise from said transmitter circuit voltage.

17. The ultrasonic diagnostic apparatus of claim 16 wherein said filter circuit further comprises an inductor and a capacitor.

18. The ultrasonic diagnostic apparatus of claim 1 wherein said transmitter power source further comprises a positive transmission voltage source and a negative transmission voltage source.

19. The ultrasonic diagnostic apparatus of claim 18 further comprising at least one charge pump circuit coupled to said at least one positive transmission voltage source for generating at least one positive bias voltage having a higher value than a positive transmission voltage.

20. The ultrasonic diagnostic apparatus of claim 18 further comprising at least one charge pump circuit coupled to said at least one negative transmission voltage source for generating at least one negative bias voltage having a higher value than a negative transmission voltage.

* * * * *